(12) United States Patent
Fu et al.

(10) Patent No.: US 10,139,160 B2
(45) Date of Patent: *Nov. 27, 2018

(54) MICROWAVE VACUUM-DRYING OF ORGANIC MATERIALS

(71) Applicant: EnWave Corporation, Vancouver, BC (CA)

(72) Inventors: Jun Fu, Port Coquitlam (CA); Timothy D. Durance, Vancouver (CA); Parastoo Yaghmaee, Vancouver (CA)

(73) Assignee: EnWave Corporation, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/942,646

(22) Filed: Apr. 2, 2018

(65) Prior Publication Data

US 2018/0224206 A1    Aug. 9, 2018

Related U.S. Application Data

(62) Division of application No. 15/087,013, filed on Mar. 31, 2016, now Pat. No. 9,958,203, which is a division (Continued)

(51) Int. Cl.
| | |
|---|---|
| *F26B 5/04* | (2006.01) |
| *A23L 5/30* | (2016.01) |
| *F26B 3/347* | (2006.01) |
| *F26B 17/04* | (2006.01) |
| *A23L 3/01* | (2006.01) |
| *A23L 3/54* | (2006.01) |

(Continued)

(52) U.S. Cl.
CPC ............ *F26B 5/048* (2013.01); *A23L 3/01* (2013.01); *A23L 3/54* (2013.01); *A23L 5/34* (2016.08); *F26B 3/347* (2013.01); *F26B 5/041* (2013.01); *F26B 17/04* (2013.01); *A23B 4/031* (2013.01); *A23B 7/02* (2013.01); *A23N 12/08* (2013.01); *A23V 2002/00* (2013.01)

(58) Field of Classification Search
CPC .... F26B 3/347; F26B 5/048; H05B 2206/046; B28B 11/241; A23L 3/54; C04B 40/0218
USPC .......................................................... 34/259
See application file for complete search history.

(56) References Cited

U.S. PATENT DOCUMENTS

| | | |
|---|---|---|
| 3,277,580 A | 10/1966 | Tooby |
| 4,020,311 A | 4/1977 | Churchland |

(Continued)

FOREIGN PATENT DOCUMENTS

| | | |
|---|---|---|
| CA | 2713382 A1 | 7/2009 |
| CN | 2870478 Y | 2/2007 |

(Continued)

*Primary Examiner* — David J Laux
(74) *Attorney, Agent, or Firm* — McKee, Voorhees & Sease, PLC

(57) ABSTRACT

An apparatus 20 for microwave vacuum-drying organic materials such as foods and bioactives has a plurality of microwave generators 50 actuated so as to cause interference between their respective microwave streams and evenly distribute the microwave energy across the vacuum chamber 34. The microwave-transparent window 36 in the chamber is arranged so the organic material to be dried is moved across it on a conveyor belt 60 and the microwave energy passing into the chamber 34 immediately encounters the organic materials, thus attenuating the energy and reducing arcing.

10 Claims, 5 Drawing Sheets

Related U.S. Application Data of application No. 13/521,410, filed as application No. PCT/CA2010/001686 on Oct. 25, 2010, now Pat. No. 9,316,437.

(60) Provisional application No. 61/295,835, filed on Jan. 18, 2010.

(51) Int. Cl.
*A23N 12/08* (2006.01)
*A23B 7/02* (2006.01)
*A23B 4/03* (2006.01)

(56) References Cited

U.S. PATENT DOCUMENTS

| | | |
|---|---|---|
| 4,045,639 A | 8/1977 | Meisel |
| 4,169,408 A | 10/1979 | Mencacci |
| 4,317,977 A | 3/1982 | Buck |
| 4,570,045 A | 2/1986 | Jeppson |
| 4,622,448 A | 11/1986 | Awata et al. |
| 4,640,020 A | 2/1987 | Wear et al. |
| 4,720,924 A | 1/1988 | Hradecky et al. |
| 4,775,770 A | 10/1988 | Fritz |
| 5,020,237 A | 6/1991 | Gross et al. |
| 5,274,859 A | 1/1994 | Redman et al. |
| 5,297,479 A | 3/1994 | Negus |
| 5,334,402 A | 8/1994 | Ovadia |
| 5,451,751 A | 9/1995 | Takimoto et al. |
| 5,892,208 A | 8/1999 | Harris et al. |
| 6,092,301 A | 7/2000 | Komanowsky |
| 6,274,859 B1 | 8/2001 | Yoshino et al. |
| 6,297,479 B1 | 10/2001 | Wefers |
| 2005/0082283 A1 | 4/2005 | Hein et al. |
| 2007/0151147 A1 | 7/2007 | Learey et al. |
| 2007/0271811 A1 | 11/2007 | Tsuruta et al. |
| 2008/0050793 A1 | 2/2008 | Durance et al. |
| 2008/0290087 A1 | 11/2008 | Ben-Shmuel et al. |

FOREIGN PATENT DOCUMENTS

| | | |
|---|---|---|
| CN | 201138123 Y | 10/2008 |
| CN | 101382379 A | 3/2009 |
| CN | 201293529 Y | 8/2009 |
| EP | 0027471 A1 | 3/1980 |
| EP | 0014121 A1 | 8/1980 |
| EP | 0113900 A1 | 11/1988 |
| EP | 0252542 A1 | 12/1990 |
| GB | 1453792 | 10/1976 |
| GB | 2071833 A | 9/1981 |
| GB | 2110803 A | 6/1983 |
| GB | 2416474 A | 2/2006 |
| JP | 2005127555 A | 5/2005 |
| WO | 9625638 A1 | 8/1996 |
| WO | 2009049409 A1 | 4/2009 |

MICROWAVE VACUUM-DRYING OF ORGANIC MATERIALS

CROSS REFERENCE

This application is a divisional of U.S. application Ser. No. 15/087,013, filed Mar. 31, 2016, which is a divisional of Ser. No. 13/521,410, filed Jul. 10, 2012, which is a 371 national phase application based on International application PCT/CA2010/001686 filed Oct. 25, 2010, which claimed the benefit of U.S. Provisional Application Ser. No. 61/295,835 filed Jan. 18, 2010; the entire contents of which are all incorporated herein by reference.

FIELD OF THE INVENTION

The invention pertains to apparatuses and methods for microwave vacuum-drying of organic materials, including food products and biologically-active materials such as vaccines, antibiotics, proteins and microorganism cultures.

BACKGROUND OF THE INVENTION

Dehydration of organic materials is commonly done in the food processing industry and in the production of biologically-active materials. It may be done in order to preserve the products for storage. It may also be done to create a product that is used in the dehydrated form, for example dried herbs and various kinds of chips. Conventional methods of dehydrating organic products include air-drying and freeze-drying. Both of these drying methods have their limitations. In general terms, air-drying is slow and freeze-drying is expensive, and both methods tend to degrade the appearance and texture of the products, which is undesirable in the case of foods.

Another method employed to dehydrate food products and biologically-active materials is microwave vacuum dehydration. Examples of this in the patent literature include WO 2009/049409 A1, Durance et al., published Apr. 23, 2009, and WO 2009/033285 A1, Durance et al., published Mar. 19, 2009. Microwave vacuum-drying is a rapid method that can yield products with improved quality compared to air-dried and freeze-dried products. Because the drying is done under reduced pressure, the boiling point of water and the oxygen content of the atmosphere are lowered, so food and medicinal components sensitive to oxidation and thermal degradation can be retained to a higher degree than by air-drying. The drying process is also much faster than air- and freeze-drying. The present invention is directed to improvements in the art of microwave vacuum-drying.

SUMMARY OF THE INVENTION

One aspect of the invention pertains to the mode of operation of microwave generators in the drying of organic materials in a vacuum chamber. The present inventors have determined that, by employing multiple microwave generators and actuating them in programmed combination and sequence, it is possible to control with precision the microwave field across a microwave transparent window. By utilizing the interference of microwaves, the invention can achieve electrically controlled microwave random scanning so that the organic materials are treated uniformly by microwave energy. This in turn permits enhanced control of the drying process.

When two or more microwave sources are operating together such that the output streams of microwaves overlap, the output streams will combine and interfere with each other in a confluent stream or beam, analogous to two rivers joining together. In the case of two microwave streams, if they are out of phase with each other, the phase shift will cause a reorientation of the confluent stream of microwaves. The inventors have determined that when multiple microwave sources are actuated and de-actuated randomly in time, the result is a random orientation of the microwave beam. This principle can be employed to randomly and evenly distribute or scan the confluent microwave stream across a defined space, without the need for mechanically reorienting the microwave generators. In the present invention the microwave stream is distributed or scanned across a microwave-transparent window for transmission of microwave radiation into a vacuum chamber containing organic material to be dehydrated. The material to be dehydrated may optionally be in movement through or within the vacuum chamber. Such movement of the material may aid in further distribution of microwave energy within the material.

The microwave chamber may incorporate a matched water load designed to absorb microwave energy that has passed through the window and through the organic material being dehydrated. The water load serves to reduce reflection of excess microwave radiation within the vacuum chamber so as to control the potential for nodes of high electric field and thus reduce the potential for arcing.

According to one aspect of the invention, there is provided an apparatus for dehydrating organic material, comprising a vacuum chamber, a set of two or more microwave generators, a microwave-transparent window for transmission of microwave radiation into the vacuum chamber, a microwave chamber between the microwave generators and the window, and means for controlling the operation of the microwave generators to actuate and de-actuate them in programmed combination and sequence, causing interference between the stream of microwaves from any one generator and the stream of microwaves from any other generator of the set.

Another aspect of the invention pertains to reducing the arcing of microwave radiation that occurs in microwave vacuum dehydrators. Arcing can cause burning of the products being dehydrated. The inventors have determined that such arcing can be reduced by an arrangement in which the organic material is placed so that radiation passing through the microwave-transparent window of the vacuum chamber immediately encounters the organic material, before passing farther into the vacuum chamber. This has the effect of attenuating the microwave energy within the vacuum chamber and thus reducing arcing. Microwave reflections caused by the organic material go back into the microwave chamber, where they can create standing waves and hot spots. Since the microwave chamber is at atmospheric pressure, the likelihood of arcing is very low. The arrangement is accomplished by placing the organic material on or close to the window, and optionally by conveying the organic material across the window, for example on a microwave-transparent conveyor belt that is on or close to the window.

According to this aspect of the invention, there is provided an apparatus for dehydrating organic material, comprising a vacuum chamber, a microwave generator, a microwave-transparent window in the vacuum chamber, a microwave chamber between the window and the generator, and optionally means for conveying the organic material across the microwave-transparent window within the vacuum chamber.

Both of the aforesaid features, i.e. the control of the microwave field and the reduction of arcing, can be incorporated into a single apparatus. According to this aspect of the invention, the apparatus includes a vacuum chamber, a set of two or more microwave generators, a microwave-transparent window in the vacuum chamber, a microwave chamber between the microwave generators and the window, the window being positioned so that the organic material can be placed on or adjacent to it such that microwave radiation passing through the window immediately encounters the organic material, and means for controlling the operation of the microwave generators to actuate and de-actuate them in programmed combination and sequence, causing interference between the stream of microwaves from any one generator and the stream of microwaves from any other generator of the set.

The invention further provides methods for dehydrating an organic material. Examples of materials suitable for dehydration by the invention include fruit, either whole, puree or pieces, either frozen or un-frozen, including banana, mango, papaya, pineapple, melon, apples, pears, cherries, berries, peaches, apricots, plums, grapes, oranges, lemons, grapefruit; vegetables, either fresh or frozen, whole, puree or pieces, including peas, beans, corn, carrots, tomatoes, peppers, herbs, potatoes, beets, turnips, squash, onions, garlic; fruit and vegetable juices; pre-cooked grains including rice, oats, wheat, barley, corn, flaxseed; hydrocolloid solutions or suspensions, vegetable gums; frozen liquid bacterial cultures, vaccines, enzymes, protein isolates; amino acids; injectable drugs, pharmaceutical drugs, natural medicinal compounds, antibiotics, antibodies; composite materials in which a hydrocolloid or gum surrounds and encapsulates a droplet or particle of a relatively less stable material as a means of protecting and stabilizing the less sensitive material; meats, fish and seafoods, either fresh or frozen, either whole, puree or pieces; dairy products such as milk, cheese, whey proteins isolates and yogurt; and moist extracts of fruits, vegetables and meats.

One aspect of the method of dehydration pertains to the mode of operation of the microwave generators. According to this aspect, the method comprises introducing the organic material into a vacuum chamber, reducing pressure in the vacuum chamber to less than atmospheric, actuating and de-actuating a set of two or more microwave generators in programmed combination and sequence, causing interference between a stream of microwaves from any one of the generators and a stream of microwaves from any other of the generators, and applying the streams of microwave radiation through a microwave-transparent window into the vacuum chamber to dehydrate the organic material, and removing the dehydrated material from the vacuum chamber.

Another aspect of the method of dehydration pertains to the reduction of the arcing of microwave radiation in a microwave vacuum dehydrator while carrying out dehydration of the organic material, such that the microwave field is attenuated by the organic material immediately upon passage through the window. According to this aspect, the method comprises introducing the organic material into a vacuum chamber, reducing the pressure to a pressure less than atmospheric, applying microwave radiation through the window to dehydrate the organic material on or close to the window, optionally conveying it through the vacuum chamber, and removing the dehydrated organic material from the vacuum chamber.

Both of the aforesaid methods can be incorporated into a single method, which includes conveying the organic material across a microwave-transparent window and also actuating and de-actuating a plurality of microwave generators in programmed combination and sequence to apply microwave radiation through the window.

These and other features of the invention will be apparent from the following description and drawings of the preferred embodiments.

DESCRIPTION OF THE PREFERRED EMBODIMENTS

Figure 1:
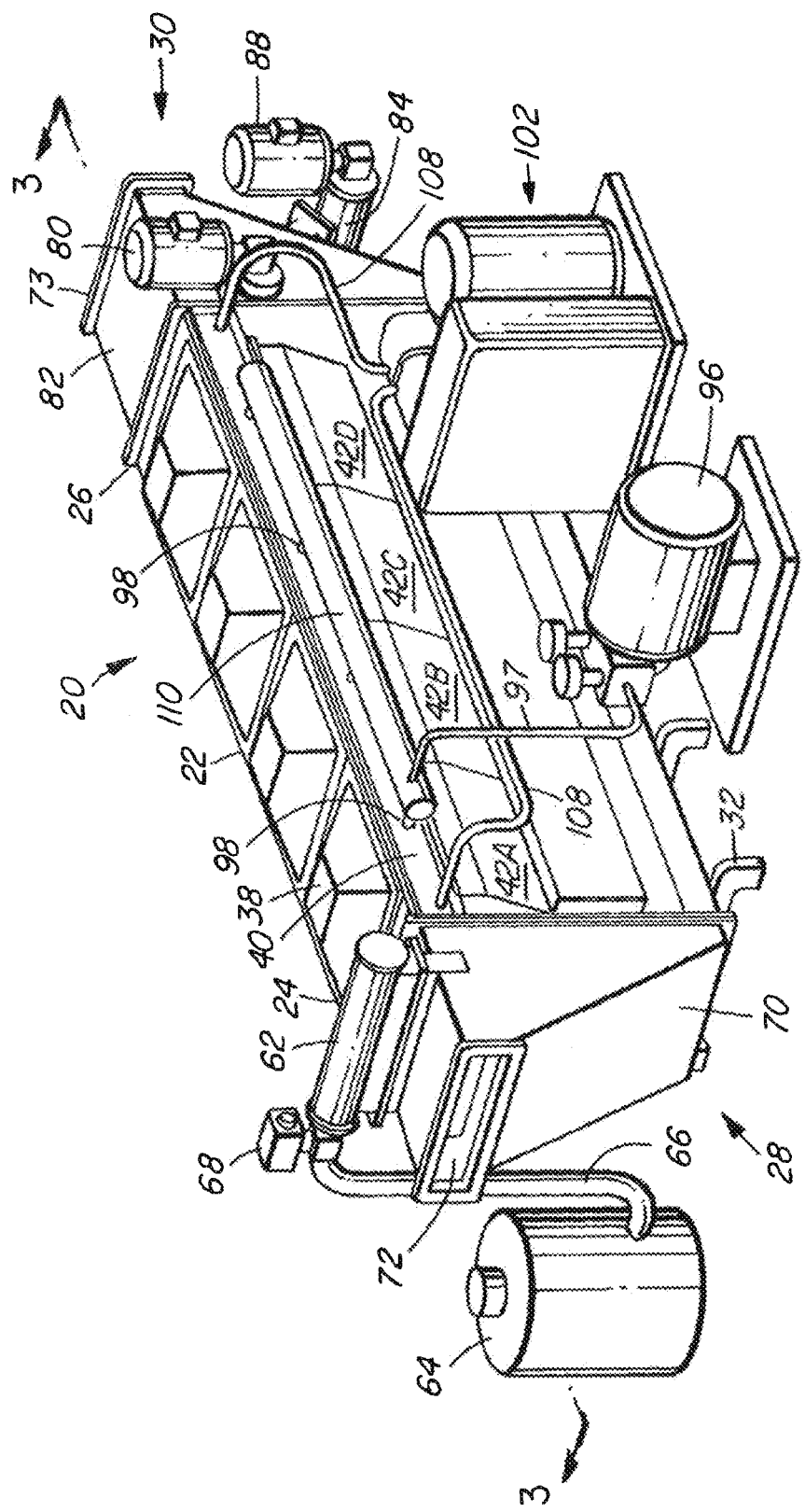
FIG. 1 is an isometric view of an apparatus according to one embodiment of the invention.
Figure 2:
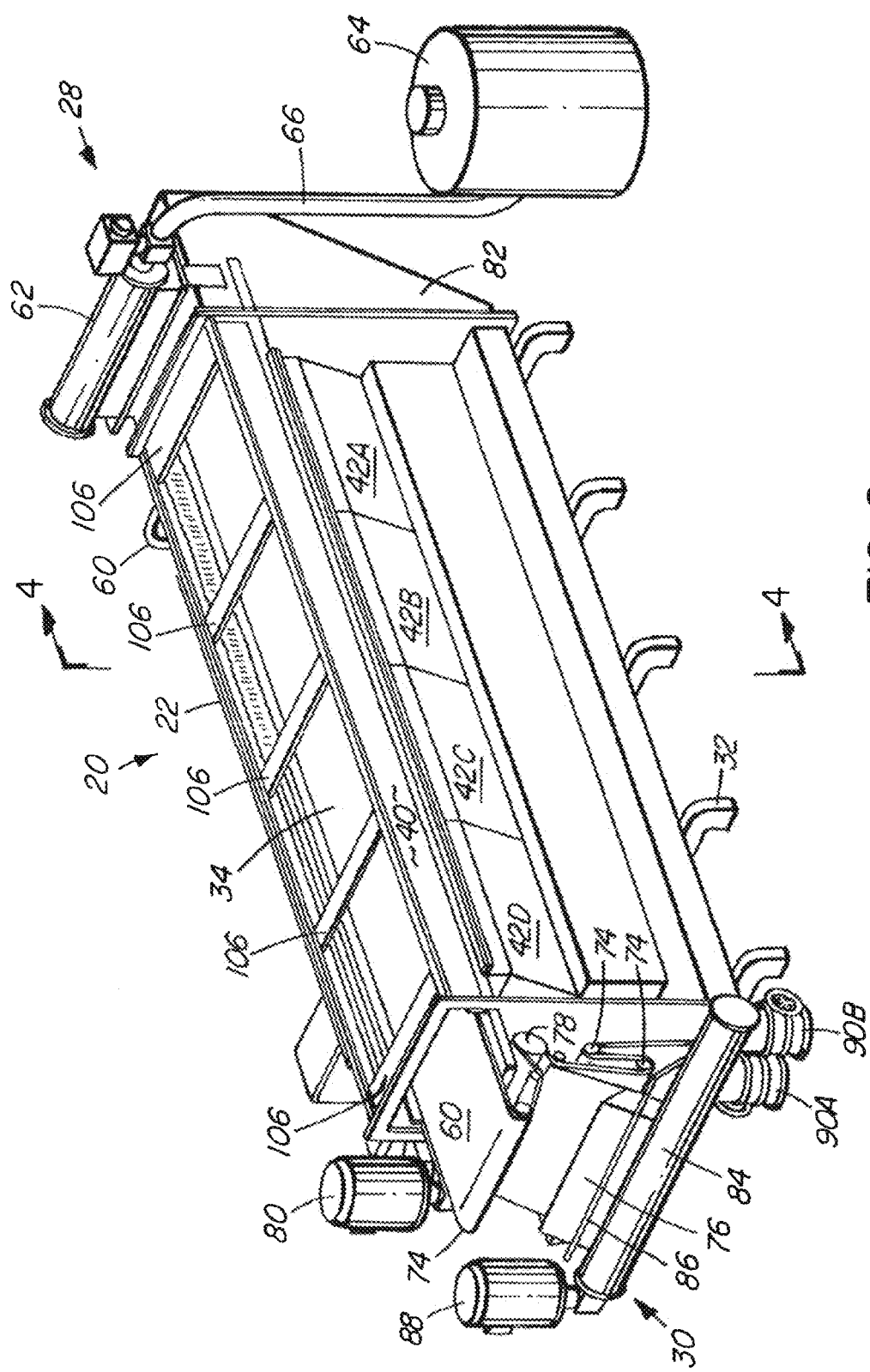
FIG. 2 is an isometric view from the opposite side of the FIG. 1 view, with the output module housing and the vacuum chamber cover removed.

Throughout the following description and the drawings, in which corresponding and like parts are identified by the same reference characters, specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

The dehydrating apparatus 20 comprises a processing unit 22, in which organic material is microwave vacuum-dried. The unit has an input end 24 and an output end 26, with a raw material loading module 28 at the input end and a dehydrated material unloading module 30 at the output end. The processing unit 22 is supported on a frame 32.

A vacuum chamber 34 extends the length of the processing unit 22. A microwave-transparent window 36, made of Teflon, forms the bottom wall of the vacuum chamber. The vacuum chamber has a cover 38 and side walls 40, with support members 106 between the walls. Microwave chamber modules are arranged below the window 36, there being four such modules 42A, 42B, 42C, 42D in the illustrated embodiment. Each module has a set of six microwave generators 50 and a microwave chamber 52. Each microwave chamber has a floor 54 with recesses 56, each accommodating a respective microwave generator 50, and two lateral side walls 58 which flare outwardly in the upward direction. The transverse side walls 59 of the microwave chambers separate the adjacent microwave chambers. The microwave-transparent window 36 forms the top wall of the microwave chambers 52. The microwave chambers are not sealed from the atmosphere and are thus air-filled and at atmospheric pressure. The microwave chambers are used to create interferential microwaves by means of space and distance.

The embodiment of FIGS. 1 to 4 has six microwave generators in each module, but the apparatus can alternatively have a different number of generators in each module, so long as there are at least two generators in each module, so that interference can occur between the waves generated by the respective generators. For example, each module may have two, three, four or more microwave generators. The generators within a module may be arranged in two or more rows with each row having two or more generators. For example, in the embodiment of FIGS. 1 to 4, there are two parallel rows (a row being oriented perpendicular to the longitudinal axis of the processing unit 22) with three generators per row. Alternatively, there may be a single row of generators in each module, perpendicular to the longitudinal axis of the processing unit, each row having two, three or more generators.

Figure 5:
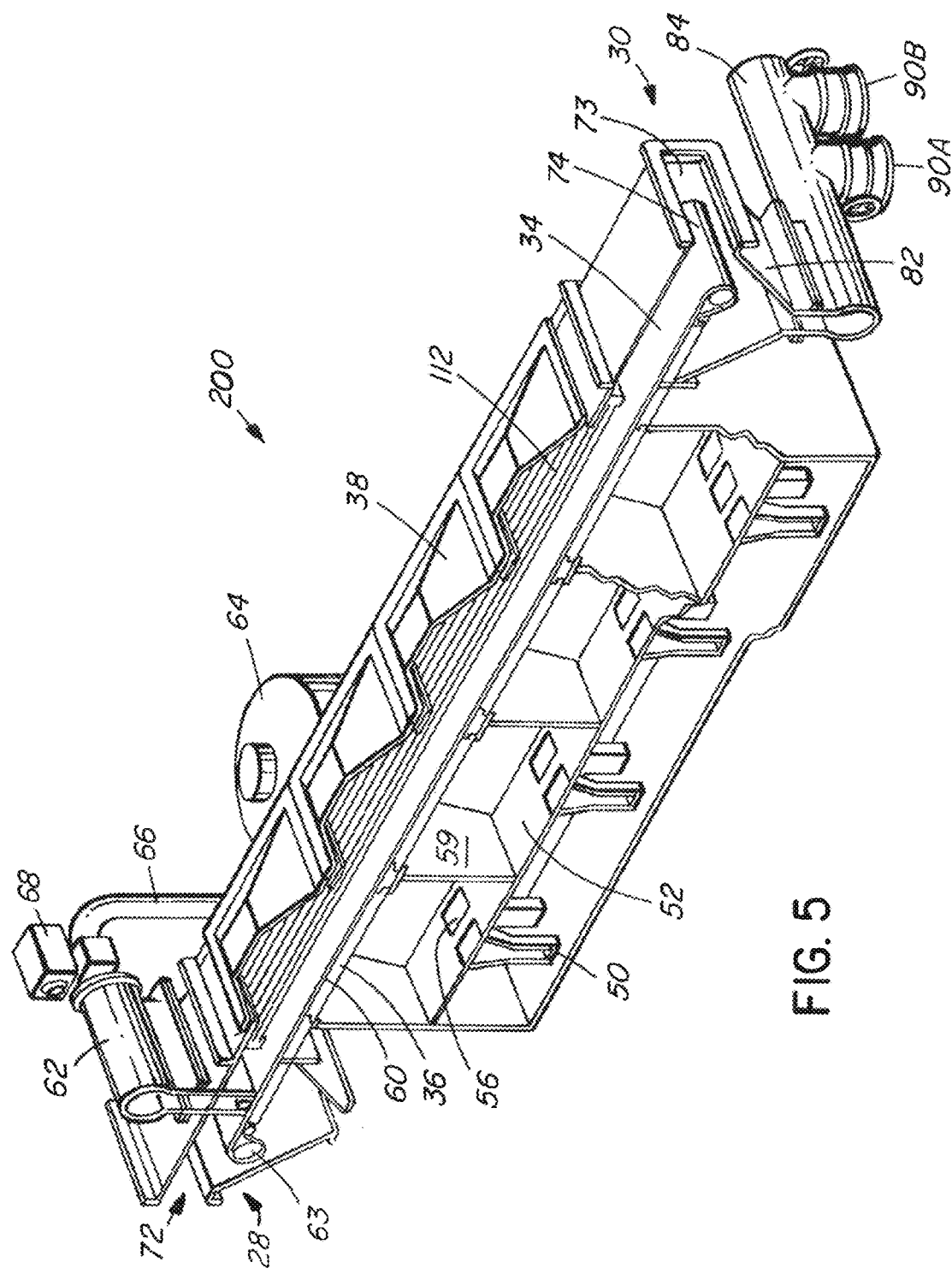
FIG. 5 is a longitudinal cutaway of another embodiment of the apparatus.

FIG. 5 illustrates an embodiment 200 of the apparatus in which there are three microwave generators 50 in each module, arranged in a single row. In all cases, the spacing between the generators within a module is selected to be such that interference will occur between the microwave streams generated by the respective generators.

A microwave-transparent conveyor belt for transport of the organic material through the vacuum chamber extends along the window 36 and is in direct contact with it. The conveyor belt extends into the loading and unloading modules 28, 30, as described below, and forms a continuous loop, for example by running below the microwave generators.

The loading module 28 has a raw material feed distributor 62 positioned above the conveyor belt 60 and configured to drop raw material to be dehydrated onto the conveyor belt. The belt runs over the conveyor rollers 63 in the loading module. A raw material supply tank 64 is connected via a feed conduit 66 to the raw material feed distributor 62. A feed controller 68 controls the flow of raw material into the distributor. The supply tank 64 is at atmospheric pressure. A raw material in liquid form for dehydration can be sucked into the distributor and vacuum chamber by the pressure differential between the vacuum chamber and the supply tank. A raw material for dehydration in the form of pieces or granules, or in open containers, may be introduced into the processing unit 22 by a conduit, auger or other transfer device capable of transporting material into the vacuum chamber without substantial loss of vacuum. For example, a series of individual open containers such as glass serum vials may be introduced into the vacuum chamber and conveyed across the window, either on a microwave-transparent belt, or directly on the window. The loading module 28 has a housing 70, fastened and sealed to the input end 24 of the processing unit. The interior of the loading module is open to the vacuum chamber and is accordingly at reduced pressure during operation of the apparatus. A viewing window 72 in the housing permits visual inspection into the vacuum chamber.

The unloading module 30 has conveyor rollers 74 for guiding the conveyor belt 60. A material collector 76 is positioned under the outward roller to receive dehydrated material that is dropped from the conveyor belt. A drive roller 78, rotated by a motor 80, drives the conveyor belt. The unloading module 30 includes a housing 82, fastened and sealed to the output end 26 of the processing unit 22 and a viewing window 73. The unloading module is open to the vacuum chamber and is thus at reduced pressure during operation of the apparatus.

Figure 3:
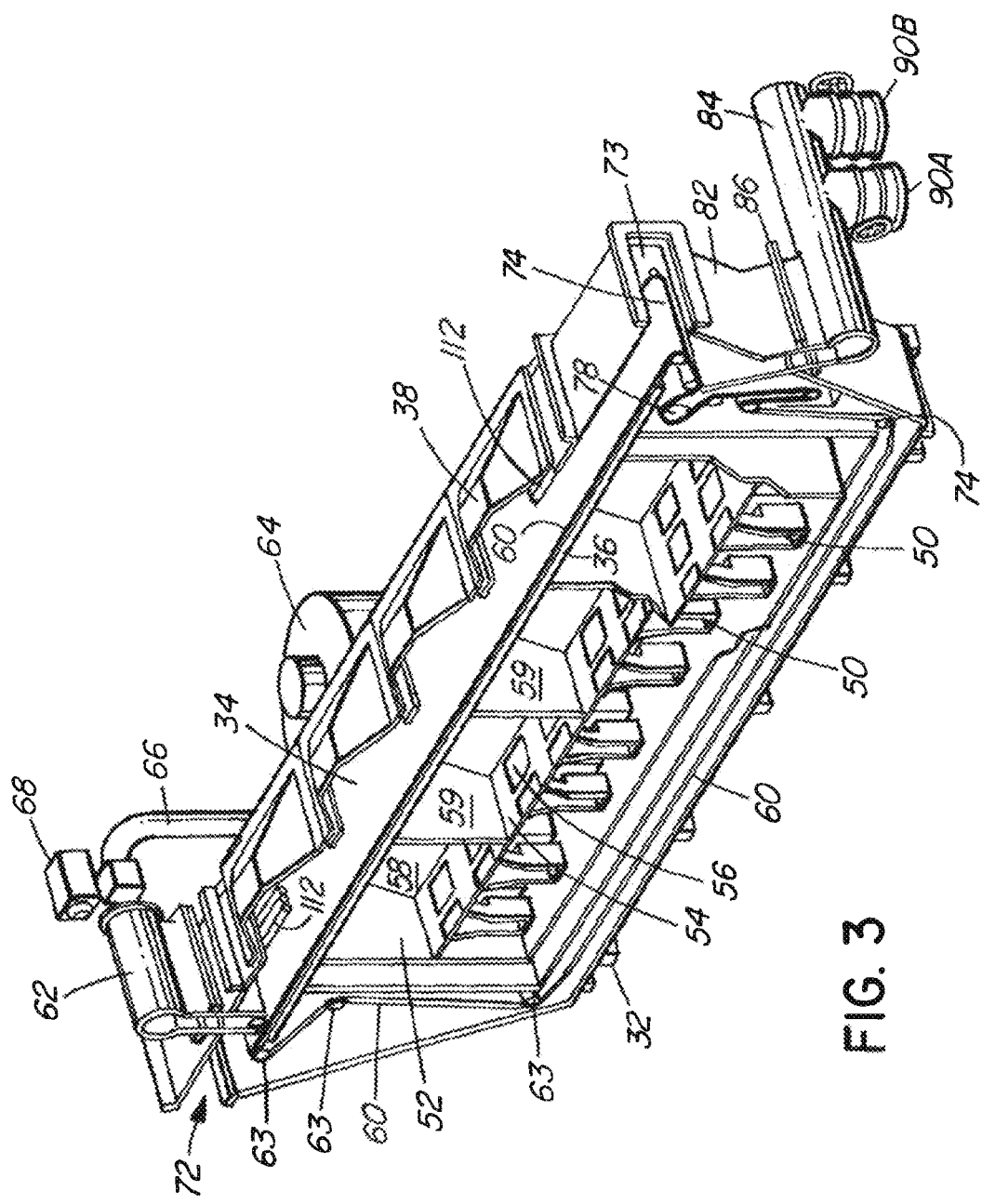
FIG. 3 is a cutaway view on the line 3-3 of FIG. 1.
Figure 4:
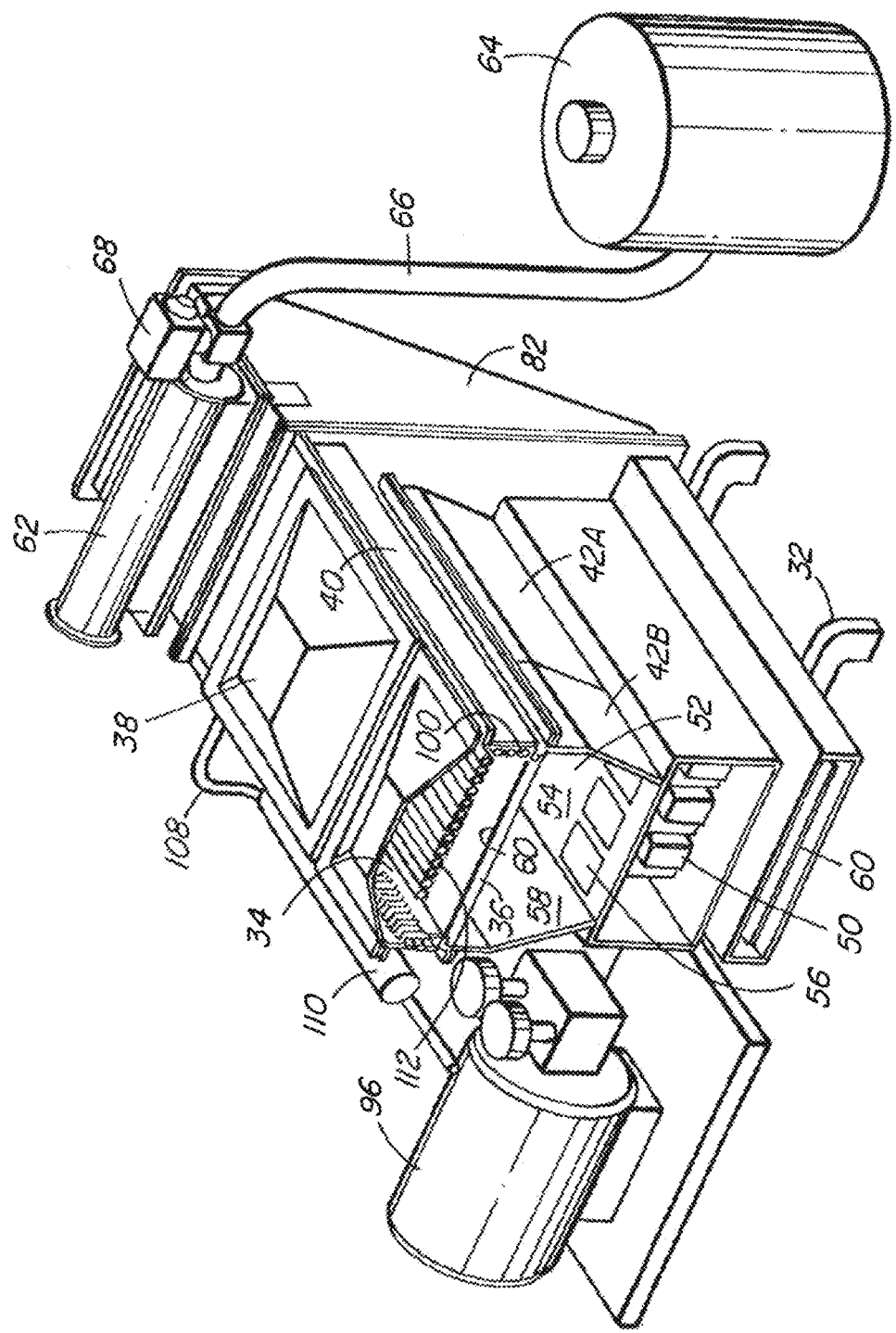
FIG. 4 is a cutaway view on the line 4-4 of FIG. 2.

Optionally, and as illustrated in FIG. 3, the conveyor belt 60 may form a continuous loop without extending below the microwave generators. Here, the conveyor belt path is around a single roller 63 in the loading module and a single roller 74 in the unloading module, with the return path of the belt being between its forward path and the microwave transparent window 36. The belt in its forward path thus lies on the belt in its return path, which in turn lies on the microwave window 36. A drive roller (not shown in FIG. 3) is provided to drive the belt.

An auger conveyor 84 is positioned under the material collector 76 and receives the dehydrated material from it. A vacuum seal 86 between the lower end of the material collector 76 and the auger conveyor 84 maintains the vacuum within the vacuum chamber 34 and auger conveyor 84. The auger 84 is driven by a motor 88. A pair of outlet valves 90A, 90B at one end of the auger conveyor provides for removal of the dehydrated material from the apparatus. The valves 90A, 90B function as an airlock to permit the removal of dried product. Vacuum-sealed containers (not shown in the drawings) to receive the dried product are attached to the valves. One valve is open at a time to permit one container to receive product from the auger, while the other valve is closed to permit removal of a filled container from that valve. The two valves are opened and closed alternately to permit the auger to run continuously.

The dehydrating apparatus includes a vacuum pump 96 operatively connected via a conduit 97 to vacuum distributor 110, which in turn connects to the vacuum chamber at vacuum ports 98 in the side walls 40 thereof. A condenser 100 is operatively connected to the refrigerator unit 102, for condensing water vapor produced during dehydration of the organic material. Alternative, the condensor may be situated outside the vacuum chamber, connected between the vacuum chamber and the vacuum pump.

The apparatus includes a refrigeration unit 102, comprising a compressor, cooling fan and refrigerant pump, connected to convey refrigerant via a refrigerant pipe 108 to the condensor 100 and thus maintain the condensor at a desired temperature.

A water load is provided at the upper part of the vacuum chamber 34 to absorb microwave energy and thus prevent reflection of microwaves in the vacuum chamber. This is accomplished by microwave-transparent water tubing 112, shown in FIG. 4, under the cover 38 of the vacuum chamber. The water that is pumped through the tubing by a pump (not shown in the drawings) can be salt or fresh water. The tubing 112 may be in various sizes and configurations to match the microwave field.

The apparatus 20 includes a programmable logic controller (PLC), programmed and connected to control the operation of the system, including controlling the inflow of feedstock, the motors, the microwave generators, the vacuum pump and the refrigerant pump. It is programmed to actuate and de-actuate the microwave generators within each of the microwave generator modules 42A to 42D. Whenever a microwave generator is actuated, the microwave created by the generator will have a new phase. Because of the microwave interference, the microwave with the new phase interferes with other microwaves and creates a new microwave distribution throughout the organic materials. Although microwave generators are actuated and de-actuated via the PLC programming, microwave phases are created randomly. The microwave distribution is thus changed randomly and frequently. Over time, the average microwave energy throughout the organic material is equalized.

For example, within a module, a given generator may be turned on at a set time for a duration of five seconds, then off for two seconds, then on for five seconds, and so on. It is preferred that at least two of the generators within a module are radiating at any given time so that the power output of the generators is higher and is available for product dehydration. The microwaves produced by any one generator are always out of phase with the microwaves produced by each other generator, due to the inherent random variation in the time at which the generators are actuated. The microwave streams thus interfere with each other to produce reinforced pulses of microwave energy which enter the vacuum chamber. The direction of the pulses varies randomly throughout the area in the chamber irradiated by the generators in a module. Over a period of time, all parts of that area are subjected to a substantially equal amount of energy.

The dehydrating apparatus 20 operates according to the following method. The vacuum pump, refrigerant pump, water pump, microwave generators, motors 80, 88 and the raw material feed controller 68 are actuated, all under the control of the PLC. Pressure within the vacuum chamber may be in the range of about 0.01 to about 100 Torr, alternatively about 0.1 to about 30 Torr. The organic material to be dehydrated is fed onto the conveyor belt 60 and is carried through the vacuum chamber across the microwave-transparent window. The material is dehydrated by the radiation from the generators passing through the window. Processing time may be in the range of about 0.5 to 2 hours. The dehydrated material falls into the material collector 76, moves into the auger conveyor 84 and is removed from the apparatus through the outlet valves 90A, 90B.

Example 1

A dehydration apparatus in the form of the apparatus 20 described above has microwave generators each having a power output of 1,200 watts. The peak power within a given microwave generator module of four generators is accordingly 4.8 kilowatts. The vacuum system evacuates the apparatus to an absolute pressure of 0.1 Torr. Each microwave chamber has a height of 14.5 inches (36.8 cm), a length of 27 inches (68.6 cm) and a width (at the top) of 28 inches (71.1 cm). The spacing between the microwave generators (center to center) is 12 inches cm) between adjacent rows and 6 inches (15.2 cm) between adjacent generators within a row. The conveyor belt is operated at a speed in the range of 0.01 to 1 centimeters per second.

Example 2

An embodiment of the invention for drying organic materials in a batch mode was operated to dehydrate various foods, bioactive materials and materials in vials, in some cases using frozen materials. The final moisture content of the dehydrated material was measured. Bulk samples of beef chunks, brussels sprouts, green peas and egg whites were dried at a pressure of 35 Torr. The results are shown in Table 1.

TABLE 1

| Sample and Weight | Drying Time | Average microwave power (W) | Final moisture content |
|---|---|---|---|
| Beef chunks (874 g) | 130 min | 1532 | 1.02 +/− 0.061% |
| Brussel (843 g) | 288 min | 973 | 4.66 +/− 1.17% |
| Green peas (759 g) | 287 min | 946 | 4.59 +/− 0.61% |
| Egg White (384 g) | 236 min | 1473 | 1.76 +/− 0.55% |

(a) Bulk samples of beef chunks, brussels sprouts, green peas and egg whites were dried at a pressure of 35 Torr. The results are shown in Table 1.
(b) Frozen samples of bioactive materials, namely lipase and amylase, were dried at a pressure of about 0.15 Torr or less. The results are shown in Table 2.

TABLE 2

| Sample and Weight | Drying Time | Average microwave power (W) | Final moisture content |
|---|---|---|---|
| Lipase (15% w/v) (337 g) | 9.5 hours | 1298 | 3.06 +/− 0.36% |
| α-amylase (15% w/v) (241 g) | 12 hours | 1071 | 2.60 +/− 0.24% |

(c) Samples of materials in vials were dried at a pressure of about 0.15 Torr or less.
The results are shown in Table 3.

TABLE 3

| Sample and Weight | Drying Time | Average microwave power (W) | Final moisture content |
|---|---|---|---|
| *Lactobacillus* (215 vials, 1 g each) | 96 min | 1118 | 2.9 +/− 0.8% |
| Skim milk solution (220 vials, 1 g each) | 168 min | 1390 | 2.05 +/− 0.01% |
| Lipase (20% w/v) (215 vials, 2 g each) | 230 min | 652 | 3.47 +/− 0.55% |

It is to be understood that, although particular means for performing certain functions of the apparatus, or particular structures or steps, have been described above in respect of the preferred embodiments, various other means, structures and steps may be employed in the apparatus and method of the invention. Examples of this include the following.
(i) The means for conveying the organic material across the microwave-transparent window can include means such as vibration of the window, sloping the window and using gravity, mechanical pushers, etc.
(ii) The means for reducing the pressure in the vacuum chamber can include any means for applying a vacuum to the vacuum chamber, such as connection to a central vacuum system of a plant.
(iii) The means for loading the organic material into the vacuum chamber and/or for unloading dehydrated material can be structured to facilitate the loading of various forms of material, e.g. solids, gels, etc., and the handling of materials in containers, for example vaccines contained in vials.
(iv) The dehydration apparatus may be structured to operate in batch mode as well as continuous mode. For batch mode, the apparatus may not require loading and unloading modules, or any conveyor for moving the organic materials through the vacuum chamber. Rather, the materials are placed in the vacuum chamber, which is then sealed and evacuated. After dehydration, the vacuum is broken, the vacuum chamber is unsealed and the dried materials are removed. Such operation may be mechanized or done manually by an operator.
(v) The processing apparatus may include any desired and practical number of modules, including a single module. The modules may be arranged in a stacked configuration in order to reduce the floorspace require by the apparatus.

LIST OF REFERENCE NUMERALS

20 dehydrating apparatus
22 processing unit
24 input end of processing unit
26 output end of processing unit
28 loading module
30 unloading module 32 frame
34 vacuum chamber
36 microwave-transparent window
38 cover of vacuum chamber
40 side walls of vacuum chamber microwave chamber
42A-D modules
50 microwave generator
52 microwave chamber
54 floor of microwave chamber
56 recesses in floor
58 side walls of microwave chamber
59 end walls of microwave chambers
60 conveyor belt
62 raw material distributor
63 conveyor belt rollers in loading module
64 raw material tank
66 feed conduit
68 feed controller
70 housing of loading module
72 viewing window of loading module
73 viewing window of unloading module
74 conveyor belt rollers in unloading module
76 material collector
78 drive roller
80 motor for drive roller
82 housing of unloading module
84 auger conveyor
86 vacuum seal in unloading module
88 motor for auger conveyor outlet control valves
90A, B
96 vacuum pump
97 vacuum conduit
98 vacuum ports in vacuum chamber side walls
100 condenser
102 refrigeration unit
106 vacuum chamber supports
108 refrigerant pipe
110 vacuum distributor
112 water load tubing
200 dehydrating apparatus

What is claimed is:

1. An apparatus for dehydrating organic material, comprising:
   (a) a vacuum chamber;
   (b) a microwave generator;
   (c) a microwave-transparent window for transmission of microwave radiation from the microwave generator into the vacuum chamber;
   (d) a microwave chamber between the microwave generator and the microwave-transparent window; and
   (e) a conveyor for conveying the organic material across the microwave-transparent window within the vacuum chamber, wherein the conveyor extends along the microwave-transparent window and in contact with the microwave-transparent window.

2. An apparatus according to claim 1, wherein the conveyor comprises a conveyor belt adjacent to the microwave-transparent window.

3. An apparatus according to claim 2, wherein the conveyor belt forms a continuous loop extending below the microwave generators.

4. An apparatus according to claim 1, further comprising a loading module for loading the organic material into the vacuum chamber.

5. An apparatus according to claim 4, further comprising an unloading module for unloading dehydrated organic material from the vacuum chamber.

6. An apparatus according to claim 5, wherein the loading module is at an input end of the apparatus and the unloading module is at an output end thereof.

7. An apparatus according to claim 1, further comprising a water load positioned in the vacuum chamber.

8. An apparatus according to claim 7, wherein the water load comprises water tubing adjacent to a top cover of the vacuum chamber.

9. An apparatus according to claim 1, further comprising a vacuum pump for reducing pressure inside the vacuum chamber.

10. The apparatus of claim 1 wherein the conveyor is microwave-transparent.

* * * * *